(12) United States Patent
Kawaguchi et al.

(10) Patent No.: US 10,049,537 B2
(45) Date of Patent: Aug. 14, 2018

(54) INFORMATION PRESENTATION APPARATUS

(71) Applicant: SONY CORPORATION, Tokyo (JP)

(72) Inventors: Hiroto Kawaguchi, Kanagawa (JP); Junji Iwasaki, Kanagawa (JP); Nobuhide Yoneya, Kanagawa (JP); Yasuhiro Watanabe, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/328,319

(22) PCT Filed: Jul. 9, 2015

(86) PCT No.: PCT/JP2015/003463
§ 371 (c)(1),
(2) Date: Jan. 23, 2017

(87) PCT Pub. No.: WO2016/021113
PCT Pub. Date: Feb. 11, 2016

(65) Prior Publication Data
US 2017/0221324 A1    Aug. 3, 2017

(30) Foreign Application Priority Data

Aug. 8, 2014 (JP) ................. 2014-163152

(51) Int. Cl.
*H04B 3/36* (2006.01)
*G08B 6/00* (2006.01)

(52) U.S. Cl.
CPC ..................... *G08B 6/00* (2013.01)

(58) Field of Classification Search
CPC .......................................... G08B 6/00
USPC .................. 340/407.1, 407.2, 965
See application file for complete search history.

(56) References Cited

U.S. PATENT DOCUMENTS

| | | | |
|---|---|---|---|
| 6,218,958 B1 * | 4/2001 | Eichstaedt | G08B 6/00 340/4.12 |
| 8,643,479 B1 * | 2/2014 | Donham | H04M 1/72547 340/407.1 |
| 2014/0316309 A1 * | 10/2014 | Seo | A61H 23/02 601/46 |

FOREIGN PATENT DOCUMENTS

| | | | |
|---|---|---|---|
| JP | 2004-147263 A | 5/2004 |
| JP | 2009-113184 A | 5/2009 |
| JP | 2011-115936 A | 6/2011 |
| TW | 201502859 A | 1/2015 |
| WO | 2014/117125 A1 | 7/2014 |

OTHER PUBLICATIONS

International Search Report and Written Opinion of PCT Application No. PCT/JP2015/003463, dated Sep. 29, 2015, 7 pages of English Translation and 6 pages of ISRWO.

(Continued)

*Primary Examiner* — Tai T Nguyen
(74) *Attorney, Agent, or Firm* — Chip Law Group

(57) ABSTRACT

An information presentation apparatus which includes an actuator, a control unit and a belt. The actuator includes a movable portion and is capable of linearly driving a movable portion. The control unit controls the actuator so that the movable portion is driven corresponding to waveform information. The belt is to attach the actuator to a user.

10 Claims, 14 Drawing Sheets

(56) References Cited

OTHER PUBLICATIONS

International Preliminary Report on Patentability of PCT Application No. PCT/JP2015/003463, dated Feb. 23, 2017, 7 pages of English Translation and 4 pages of IPRP.

* cited by examiner

INFORMATION PRESENTATION APPARATUS

CROSS REFERENCE TO RELATED APPLICATIONS

This application is a U.S. National Phase of International Patent Application No. PCT/JP2015/003463 filed on Jul. 9, 2015, which claims priority benefit of Japanese Patent Application No. JP 2014-163152 filed in the Japan Patent Office on Aug. 8, 2014. Each of the above-referenced applications is hereby incorporated herein by reference in its entirety.

TECHNICAL FIELD

The present technology relates to an information presentation apparatus that presents information to a user by using tactile stimulation.

BACKGROUND ART

A mechanism that notifies a user of occurrence of some kind of event by using tactile stimulation caused by vibration or the like has already been introduced into many portable apparatuses. For example, in a watch type electronic apparatus, a vibration generation source provided in the watch body is driven when the set time has come, the vibration is transmitted to the arm of the user, and thus, such an event that the set time has come is provided to the user by tactile stimulation. This kind of electronic apparatus often uses a vibration motor including a weight such as a balance weight provided eccentrically to the rotation shaft as a vibration generation source (see, for example Patent Literature 1).

CITATION LIST

Patent Literature

Patent Literature 1: Japanese Patent Application Laid-open No. 2011-203277

DISCLOSURE OF INVENTION

Technical Problem

Most of the information presentation apparatuses that present information to a user by using tactile stimulation caused by vibration or the like have not reach the level at which various kinds of information are simply presented. For that reason, there are still many points expected to be improved, which are desired to be solved.

In view of the circumstances as described above, it is an object of the present technology to provide an information presentation apparatus capable of favorably presenting information to a user by using tactile stimulation.

Solution to Problem

In order to solve the above-mentioned problem, an information presentation apparatus according to a first embodiment of the present technology includes an actuator that includes a movable portion and is capable of linearly driving the movable portion; a control unit that controls the actuator so that the movable portion is driven corresponding to waveform information; and a belt for attaching the actuator to a user.

Specifically, in this information presentation apparatus, the actuator linearly drives the movable unit corresponding to the waveform of the given waveform information. Information is transmitted by tactile stimulation given to a user due to the linear movement of the movable unit.

An end portion of the belt may be fixed to the movable portion, and the information presentation apparatus may be configured so that a length of a portion of the belt is changed by driving of the movable portion in a forward or backward direction, the portion being wrapped around the user, The information presentation apparatus may further include a communication unit that acquires setting information through communication, the setting information including at least stimulation-type information for identifying a kind of the tactile stimulation, in which the control unit may be configured to generate the waveform information on the basis of the stimulation-type information included in the acquired setting information.

Accordingly, it is possible to give various kinds of tactile stimulation to a user.

The setting information may further include temporal setting information, and the control unit may be configured to generate a timing of driving the movable portion on the basis of the temporal setting information included in the acquired setting information.

The information presentation apparatus may further include a pressing portion that is freely movable forward and backward in approaching and separating directions with respect to an attached portion of the user in synchronization with the movable portion.

Specifically, in this information presentation apparatus, information caused by a feeling of pressure is presented to a user by the movement of the pressing unit in forward and backward directions.

In order to solve the above-mentioned problem, an information presentation apparatus according to a second embodiment of the present technology includes a plurality of actuators, each of the plurality of actuators including a movable portion and is capable of linearly driving the movable portion; a control unit that controls the plurality of actuators so that the movable portion is driven corresponding to waveform information; and a belt for attaching the plurality of actuators to a user.

The belt may include a plurality of coupling belts for coupling the plurality of actuators to each other in series, an end portion of the respective coupling belts being fixed to the movable portion of the respective first actuators, and the information presentation apparatus may be configured so that a length of a portion of the belt may be changed in synchronization with driving of the movable portion of at least a part of the actuators, the portion being wrapped around the user, Further, in this information presentation apparatus, each of the plurality of actuators may further include a pressing portion that is freely movable forward and backward in approaching and separating directions with respect to an attached portion of the user in synchronization with the movable portion.

Advantageous Effects of Invention

As described above, according to the present technology, it is possible to favorably present information to a user by using tactile stimulation.

It should be noted that the effect described here is not necessarily limitative and may be any effect described in the present disclosure.

BRIEF DESCRIPTION OF DRAWINGS

FIG. 12 An overall side view of a wearable apparatus 100a configured by using the actuator 1a.

FIG. 14 An overall side view of a wearable apparatus 100b configured by using one actuator 1a.

MODE(S) FOR CARRYING OUT THE INVENTION

Hereinafter, embodiments of the present technology will be described with reference to the drawings.
<First Embodiment>

A first embodiment in the case where an information presentation apparatus according to the present technology is used as a wearable apparatus that is an electronic apparatus worn by a user for use will be described.

This wearable apparatus is an apparatus that has a function of presenting, for example, information related to time to the user. Note that the information related to time represents information on a general event related to time such as information (alarm) presenting that the set time has come and information presenting the remaining time before the set time.

As a mechanism that presents the information related to time to a user, an auditory presentation method with electronic sound or the like and a visual presentation method with a display are generally used.

However, sound has a high diffusivity and can be transmitted to other people, which may lead to a noise problem. For that reason, the magnitude of sound needs to be reduced for use in, for example, a public place, and thus, the performance for presenting information is limited. On the other hand, the method of visually presenting time information to a user by using a display or the like needs an action to actively look at the display, which is performed by a user. Therefore, there is a wall that is difficult to overcome with regard to alarm performance.

In the wearable apparatus according to this embodiment, the information related to time is tactually presented to a user. Note that a tactile sense represents a general sense perceived when it occurs on a body surface. For example, there are various kinds of tactile senses such as a pressed tactile sense (feeling of pressure), rubbed tactile sense (feeling of rubbing), hit tactile sense (feeling of hitting), and tightened tactile sense (feeling of tightness).

The presentation of information using a tactile sense has advantages that unintended spread of information, which causes a noise problem or the like, is unlikely to occur, and information can be presented without a user's active action of confirmation. Further, the wearable apparatus according to this embodiment employs a mechanism that presents information by using a tactile sense in such a way that a user can intuitively understand the attribution of the information such as meaning and importance of the information.

Hereinafter, a wearable apparatus according to a first embodiment of the present technology will be described with reference to the drawings.

[Configuration of Wearable Apparatus]

Figure 1:
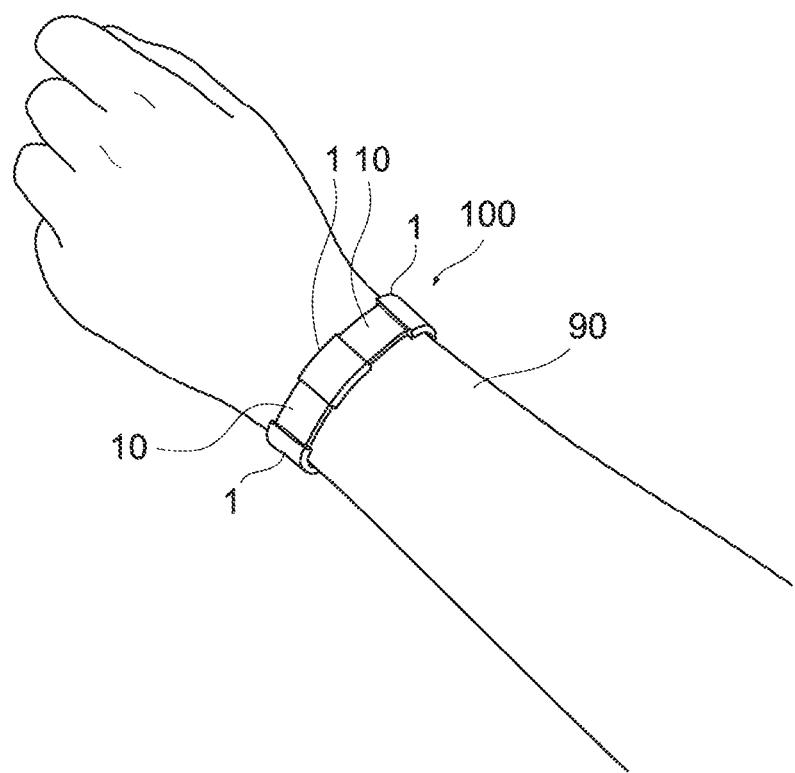
FIG. 1 A perspective view showing a wearable apparatus according to a first embodiment of the present technology.

FIG. 1 is a perspective view showing the wearable apparatus according to this embodiment.

As shown in the figure, a wearable apparatus 100 according to this embodiment is assumed to be a bracelet-type apparatus that can be attached to an attachment portion such as a wrist of a human (user).

However, the present technology is not limited to a bracelet-type one, and may be those configured to be attached to various attachment portions from which a tactile sense can be obtained, such as neck, ankle, body, and head.

The wearable apparatus 100 shown in FIG. 1 includes a plurality of actuators 1 and a plurality of belts 10 (coupling belts) that couple the actuators to each other in series so that one bracelet is formed as a whole. The plurality of actuators 1 may have the same configuration. The plurality of actuators 1 are coupled to each other at, for example, regular intervals via the belts 10.

Note that the wearable apparatus according to the present technology may include one actuator 1 and one belt 10.

Figure 2:
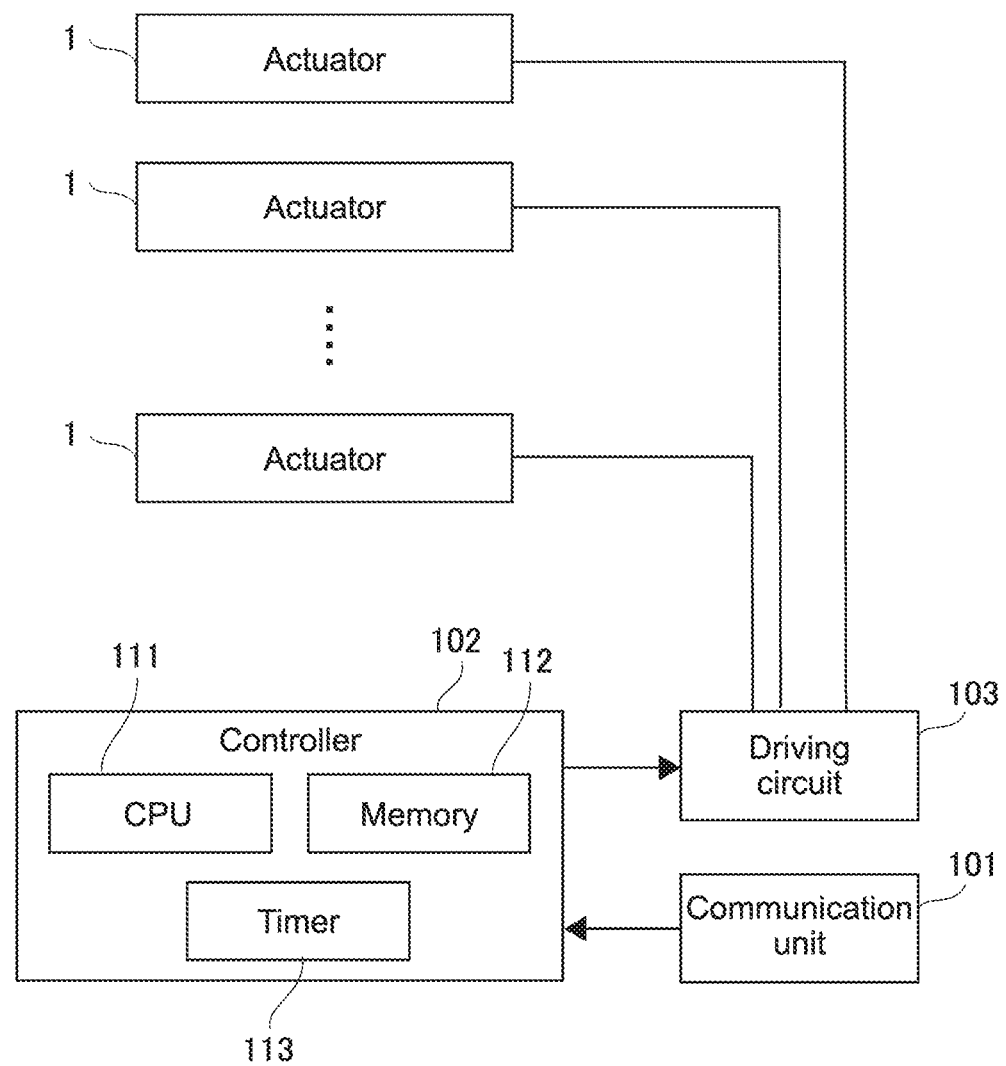
FIG. 2 A block diagram showing the electrical configuration of a wearable apparatus 100 according to the first embodiment.

FIG. 2 is a block diagram showing the electrical configuration of the wearable apparatus 100 according to this embodiment.

The wearable apparatus 100 according to this embodiment includes the plurality of actuators 1, . . . , 1, a communication unit 101, a controller 102, a driving circuit 103, a battery (not shown), and the like.

Note that the communication unit 101, the controller 102, the driving circuit 103, and an electronic part such as a battery (not shown) may be mounted on any one of the actuators or a dedicated unit.

The actuator 1 has a mechanism that generates mechanical displacement for tactile stimulation and is capable of linearly driving the movable portion in a forward or backward direction. In the wearable apparatus 100 according to this embodiment, any one of "a feeling of pressure" felt by a user and "a feeling of tightness" is used as tactile stimulation, for example. The "feeling of pressure" is obtained by causing a pressing part to move forward and backward toward the surface of a wrist of the user to press the surface of the wrist of the user. The "feeling of tightness" is obtained by increasing and decreasing the length of a portion of the belt 10, which is wrapped around the wrist of the user, to tighten and loosen the wrist. The structure of the actuator that is capable of giving such tactile stimulation will be described later.

The driving circuit 103 generates driving current to be supplied to the actuators 1 on the basis of a control signal from the controller 102.

The communication unit 101 performs wired or wireless communication between the communication unit 101 and an information processing terminal of a user, such as a mobile phone, a personal computer, a smartphone, and a tablet terminal.

The controller 102 includes a CPU 111, a memory 112, and a timer 113.

The CPU 111 stores alarm setting information, which has been transmitted from the information processing terminal of the user via the communication unit 101, in the memory 112. The alarm setting information will be described later.

The CPU 111 generates a timing of emitting alarm and waveform information of the alarm on the basis of the current date and time of the timer 113 and the alarm setting information, and outputs a control signal to the driving circuit 103 so that driving current corresponding to the waveform information is supplied from the driving circuit 103 to the actuator 1.

The battery is a source of power supply necessary for causing the electrical element of the wearable apparatus 100 to operate.

[Structure of Actuator 1]

Next, a structural example of the actuator 1 that is capable of giving tactile stimulation caused by a feeling of pressure will be described.

Figure 3:
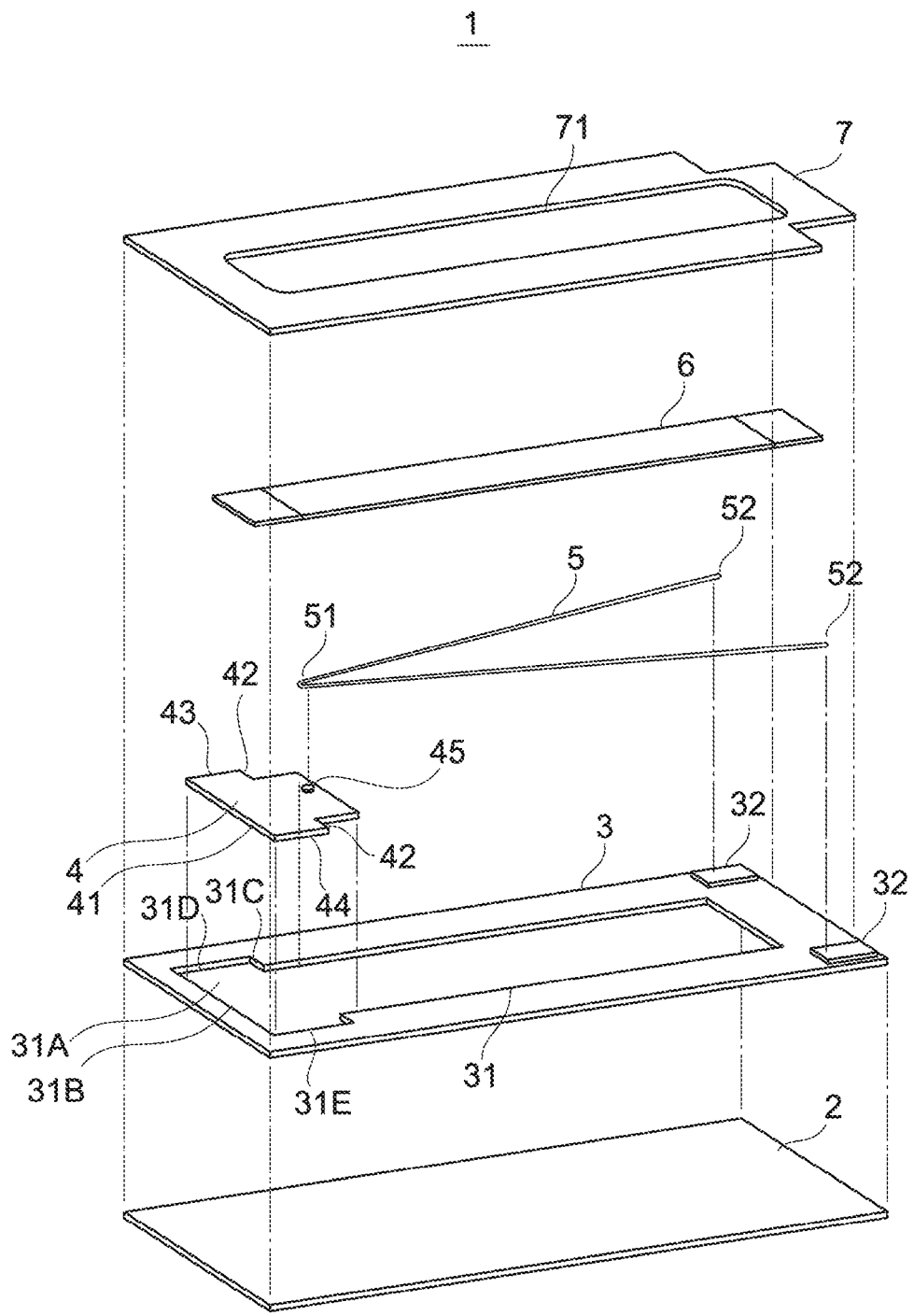
FIG. 3 An exploded perspective view showing the configuration of an actuator 1 according to the first embodiment.

FIG. 3 is an exploded perspective view showing the configuration of the actuator 1 according to the first embodiment.

Figure 4:
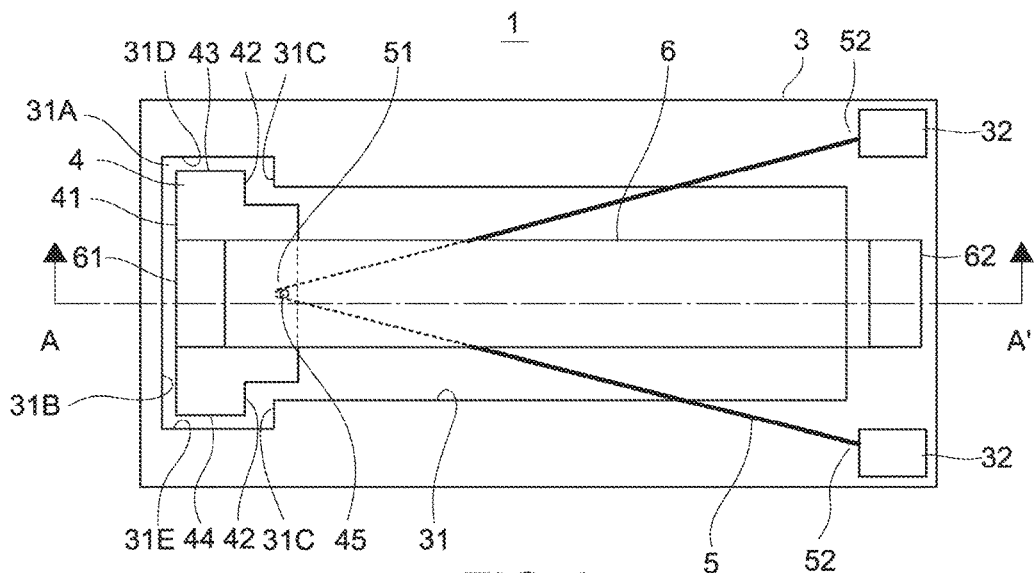
FIG. 4 A plan view showing the configuration of the actuator 1 in FIG. 3 excluding a base plate 2 and a top plate 7.

FIG. 4 is a plan view showing the configuration of the actuator 1 in FIG. 3 excluding a base plate 2 and a top plate 7.

Figure 5:
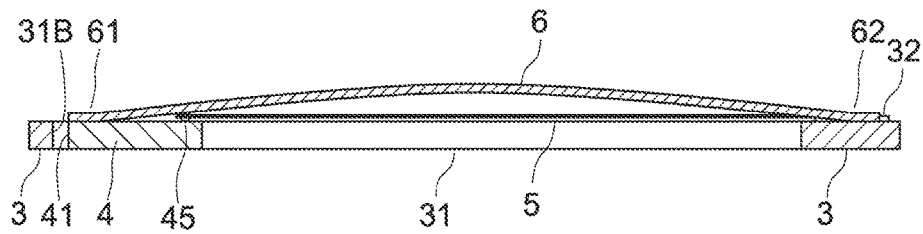
FIG. 5 A cross-sectional view of the actuator 1 in FIG. 3.

FIG. 5 is a cross-sectional view of the actuator 1 in FIG. 3 and FIG. 4.

As shown in these figures, this actuator 1 includes the base plate 2, a holder 3, a slider 4 (movable portion), a shape-memory alloy wire 5, an elastic plate 6 (pressing portion), and the top plate 7.

The base plate 2 is formed of, for example, a rectangular thin plate member. On the base plate 2, the holder 3 is fixed.

The holder 3 is formed of, for example, a rectangular thin plate member. In the holder 3, an opening portion 31 is formed. One end portion of the opening portion 31 in an X-axis direction is used as a slider holding space 31A in which the slider 4 is slidably held in the X-axis direction. In more detail, the slider 4 has a thickness similar to that of the holder 3, and is three-dimensionally held in the three-dimensional space formed by the slider holding space 31A of the holder 3, the upper surface of the base plate 2, and the lower surface of the top plate 7.

The inner wall surface of the slider holding space 31A of the holder 3 functions as stopper surfaces 31B and 31C and slide guide surfaces 31D and 31E. The stopper surfaces 31B and 31C are respectively brought into contact with end surfaces 41 and 42 of the slider 4 in the X-axis direction to limit the sliding range. The slide guide surfaces 31D and 31E are respectively brought into contact with end surfaces 43 and 44 of the slider 4 in a Y-axis direction to guide the sliding.

The shape-memory alloy wire 5 is a wire formed of a shape-memory alloy. In this embodiment, one shape-memory alloy wire 5 bent in a V-shape at a central portion 51 is used. The central portion 51 of the shape-memory alloy wire 5 is locked at a locking portion 45 provided to the slider 4. End portions 52, 52 of the shape-memory alloy wire 5 are bonded to a pair of electrode units 32, 32 provided on the upper surface of the holder 3. Specifically, the shape-memory alloy wire 5 is placed to be pulled across a surface in parallel with the sliding surface of the slider 4. The pair of electrode units 32, 32 is provided on the surface of one end portion of the holder 3 in the X-axis direction. On the other end portion of the holder 3 in the X-axis direction, the slider holding space 31A is provided. In more detail, the pair of electrode units 32, 32 is provided at positions away from each other from the central position of the holder 3 in the Y-axis direction on the surface of the one end portion of the holder 3.

Figure 6:
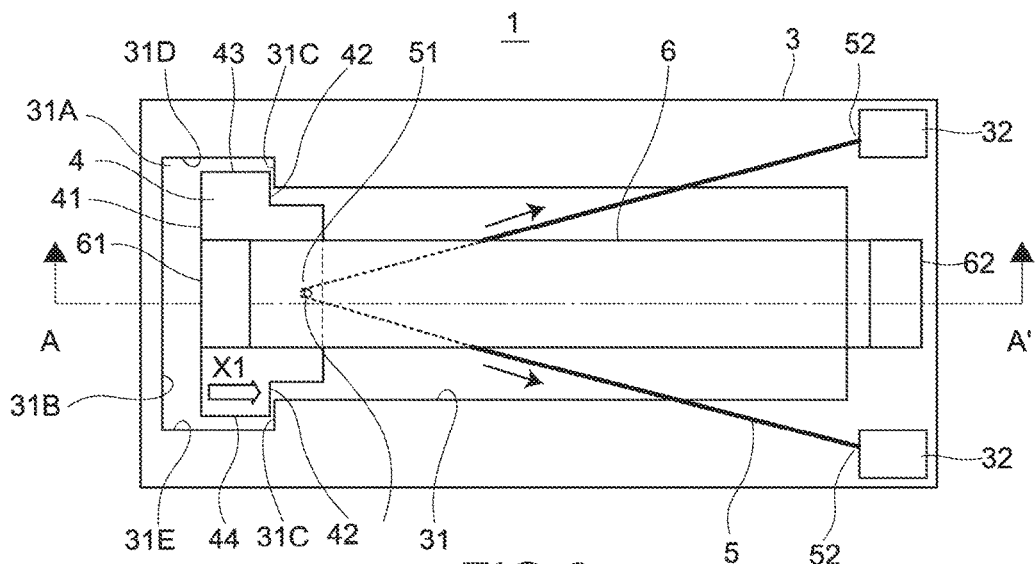
FIG. 6 A plan view showing the actuator 1 when being energized.
Figure 7:
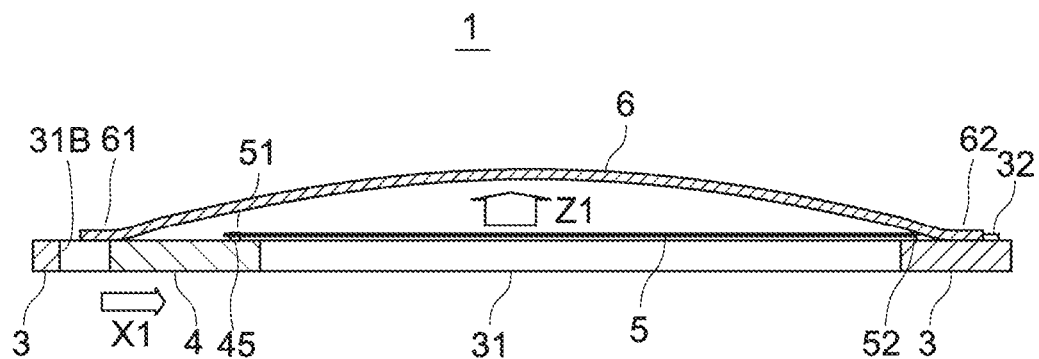
FIG. 7 A cross-sectional view showing the actuator 1 when being energized.

To the shape-memory alloy wire 5, current flows from a driving circuit (not shown) via the pair of electrode units 32, 32. When the temperature of the shape-memory alloy wire 5 has reached a predetermined temperature (specific temperature) by the joule heat generated by the current flowing through the shape-memory alloy wire 5, the shape-memory alloy wire 5 contracts in a line length direction. Since the central portion 51 of the shape-memory alloy wire 5 is locked at the locking portion 45 provided to the slider 4, the slider 4 is pulled toward the side of the bonding points of the end portions 52, 52 of the shape-memory alloy wire 5, and slides in an X1 direction in the slider holding space 31A when the shape-memory alloy wire 5 contracts in the line length direction, as shown in FIG. 6 and FIG. 7.

Further, when the energization to the shape-memory alloy wire 5 is stopped and the temperature of the shape-memory alloy wire 5 falls below the predetermined temperature (specific temperature), the shape-memory alloy wire 5 restores the original length before contraction. As a result, the slider 4 slides in the slider holding space 31A of the holder 3 in a direction opposite to the X1 direction and returns to the position shown in FIG. 4 and FIG. 5.

The elastic plate 6 (pressing portion) is formed of a thin plate elastic member. An end portion 61 of the elastic plate 6 is fixed to the slider 4, and the other end portion 62 of the elastic plate 6 is fixed to the one end portion of the holder 3 in the X-axis direction. On the other end portion of the holder 3 in the X-axis direction, the slider holding space 31A is provided.

The distance between the fixed points of the elastic plate 6 is changed along with sliding of the slider 4 in the X-axis direction. When the shape-memory alloy wire 5 is energized, the slider 4 slides in the slider holding space 31A in the X1 direction, and the distance between the fixed points of the elastic plate 6 is decreased. At this time, the elastic plate 6 is elastically deformed in a Z1 direction as shown in FIG. 7 by receiving pressure from the side of the fixed points, and thus is in a predetermined warped state.

In this actuator 1, slight warpage in the direction toward the top plate 7 (in the Z1 direction) is given to the elastic plate 6 as the initial distortion when the slider 4 is located at the position where the shape-memory alloy wire 5 is not energized (position shown in FIG. 4 and FIG. 5). Accordingly, it is possible to reliably make the elastic plate 6 in a predetermined warped state in which the elastic plate 6 is elastically deformed in the direction toward the top plate 7 (in the Z1 direction), when the shape-memory alloy wire 5 is energized.

When the slider 4 slides in the slider holding space 31A in the direction opposite to the X1 direction after the energization to the shape-memory alloy wire 5 is stopped, the distance between the fixed portions of the elastic plate 6 is increased. As a result, the elastic plate 6 returns to a slight warped state by the initial distortion.

The top plate 7 is formed of, for example, a rectangular thin plate member. At the position of the top plate 7, which substantially faces the elastic plate 6, an opening portion 71 is provided. This opening portion 71 is a portion for making at least a part of the elastic plate 6 in the predetermined warped state when the shape-memory alloy wire 5 is energized project to the position higher than the upper surface of the top plate 7.

As described above, in this actuator 1, it is possible to make the slider 4 slide by the movement of the contraction of the shape-memory alloy wire 5 in the line length direction when being energized, elastically deform the elastic plate 6 by decreasing the distance between the fixed points of the elastic plate 6 whose one end is fixed to this slider 4, and generate displacement in a direction perpendicular to the sliding surface of the slider 4 (in the Z-axis direction). That is, with a little number of parts, it is possible to generate displacement for elastically deforming the elastic plate 6 by the movement of the contraction of the shape-memory alloy wire.

Further, because this actuator 1 includes the base plate 2, the holder 3, the slider 4, the elastic plate 6, and the top plate 7 combined in the plate thickness direction, which are each formed of a thin plate member, and the shape-memory alloy wire 5 is placed to be pulled across the surface direction of the plate parts, it is possible to achieve a thickness reduction and size reduction.

Figure 8:
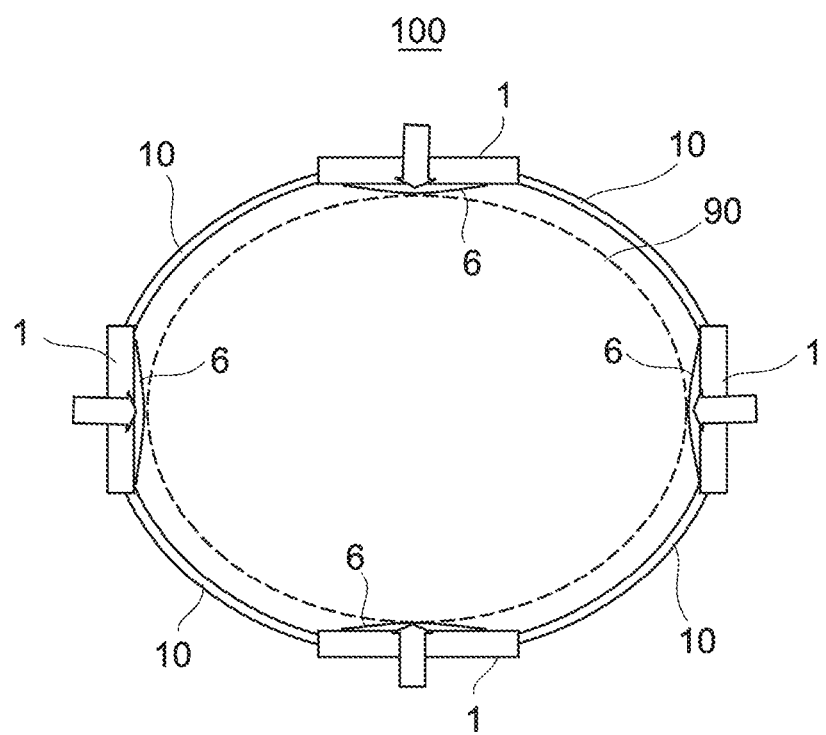
FIG. 8 An overall side view of the wearable apparatus 100 configured by using the actuator 1.

FIG. 8 is an overall side view of the wearable apparatus 100 configured by using the actuator 1.

The actuators 1 are coupled to each other by the belts 10 in series so that elastic plates 6 project toward the inside of the loop by being elastically deformed when it is attached to a wrist 90 of a user.

The controller 102 outputs a control signal to the driving circuit 103 so that driving current is supplied to the actuators 1 at the same time. Accordingly, the elastic plates 6 of the actuators 1 are elastically deformed in synchronization with each other, and tactile stimulation caused by a feeling of pressure is concurrently given to the wrist 90 of the user.

Next, a structural example of an actuator 1a that is capable of giving tactile stimulation caused by a feeling of tightness will be described.

Figure 9:
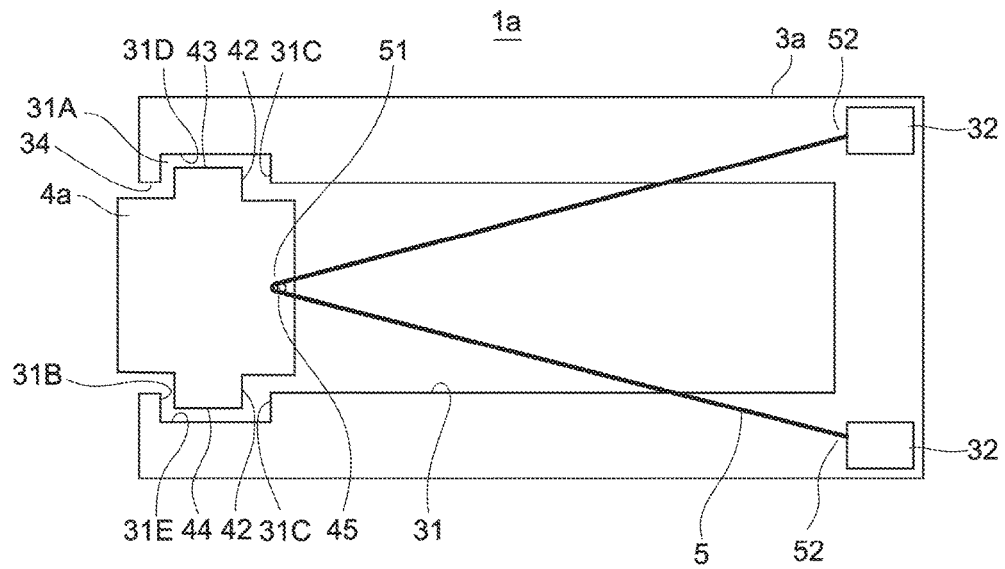
FIG. 9 A plan view showing the configuration of an actuator 1a that is capable of giving tactile stimulation caused by a feeling of tightness.
Figure 10:
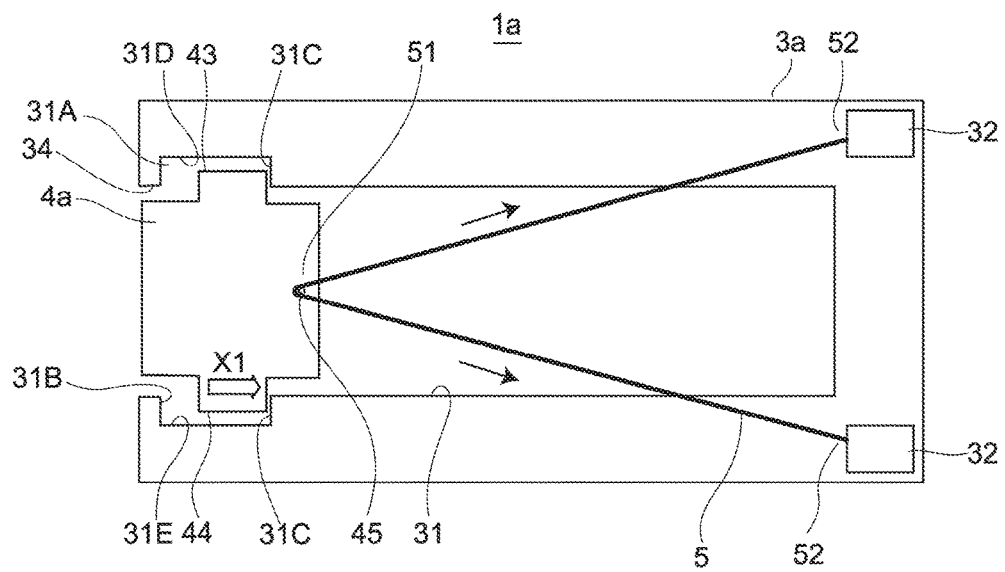
FIG. 10 A plan view showing the actuator 1a when being energized.

FIG. 9 and FIG. 10 are each a plan view showing the configuration of the actuator 1a that is capable of giving tactile stimulation caused by a feeling of tightness.

This actuator 1a is configured so that the sliding displacement of a slider 4a is made to be an output of the actuator 1a.

Specifically, in this actuator 1a, when the shape-memory alloy wire 5 is energized, the shape-memory alloy wire 5 contracts in the line length direction as shown in FIG. 10, and the slider 4a slides the slider holding space 31A in the X1 direction by being pulled toward the side of the bonding portions of the end portions 52, 52 of the shape-memory alloy wire 5.

When the energization to the shape-memory alloy wire 5 is stopped and the temperature of the shape-memory alloy wire 5 falls below a predetermined temperature (specific temperature), the shape-memory alloy wire 5 restores the original length before contraction. As a result, the slider 4a slides in the slider holding space 31A of a holder 3a in the direction opposite to the X1 direction, and returns to the position shown in FIG. 9.

Figure 11:
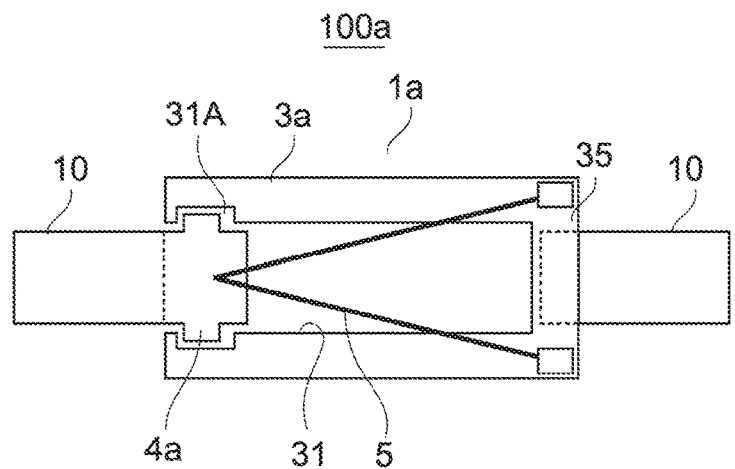
FIG. 11 A plan view showing the connection structure of an actuator 1a and a belt 10.

FIG. 11 is a plan view showing the connection structure of this actuator 1a and the belt 10.

As shown in the figure, one end portion of the belt 10 is connected to an end portion of the slider 4a of the actuator 1a in the X-axis direction, and the other end portion of the belt 10 is connected to an end portion 35 of the holder 3a opposite to the end portion to which the slider holding space 31A is provided. Accordingly, the wearable apparatus 100a in which the actuator 1a and the belt 10 forms one loop is configured.

Figure 12:
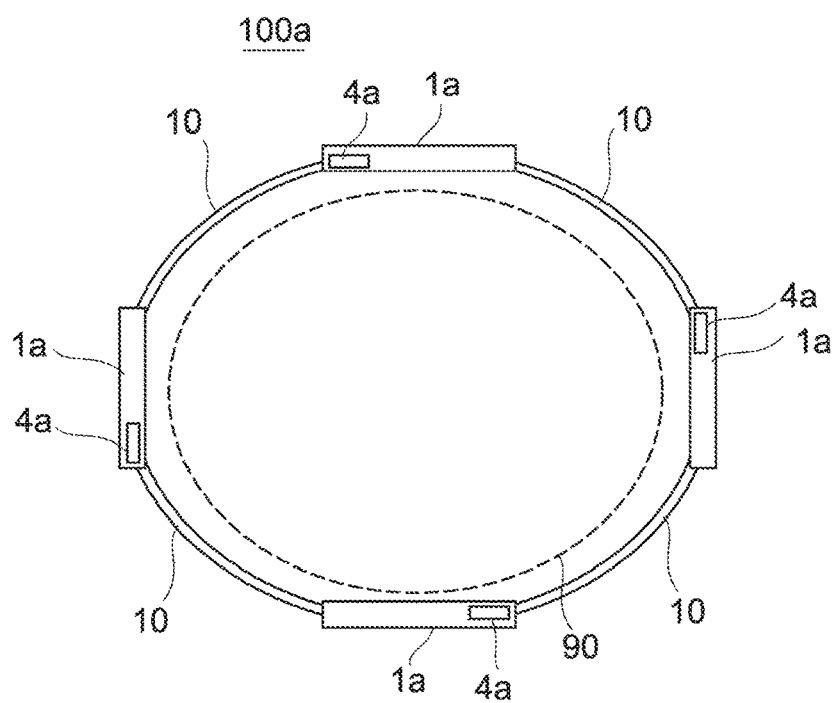
Figure 13:
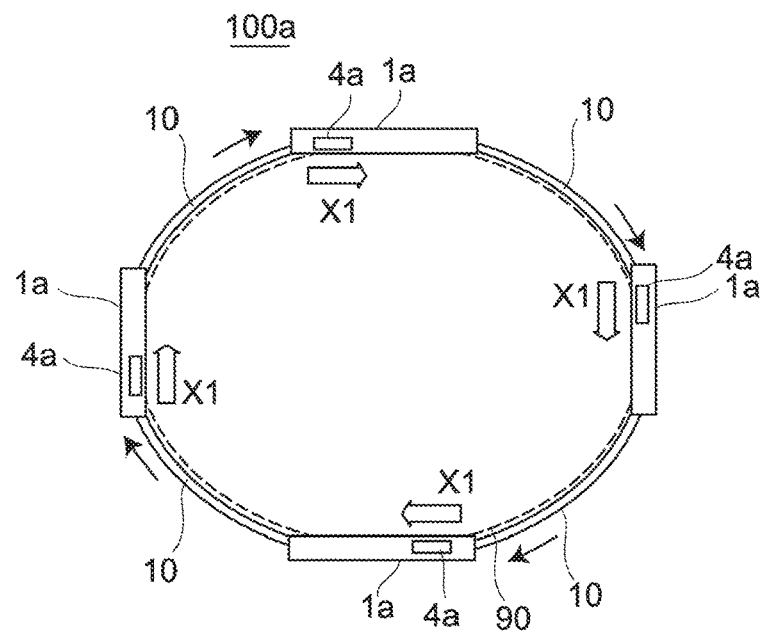
FIG. 13 An overall side view showing the wearable apparatus 100a when being energized in FIG. 12.

In this the wearable apparatus 100a, the slider 4a slides in the slider holding space 31A in the X1 direction when the shape-memory alloy wire 5 is energized, thereby reducing the whole length of the loop, i.e., the length of the portion wrapped around the wrist 90 of the user, as shown in FIG. 12 and FIG. 13. As a result, the wrist 90 is tightened. This feeling of tightness is given to the human as information such as notification of occurrence of some kind of event and content of the event.

Figure 14:
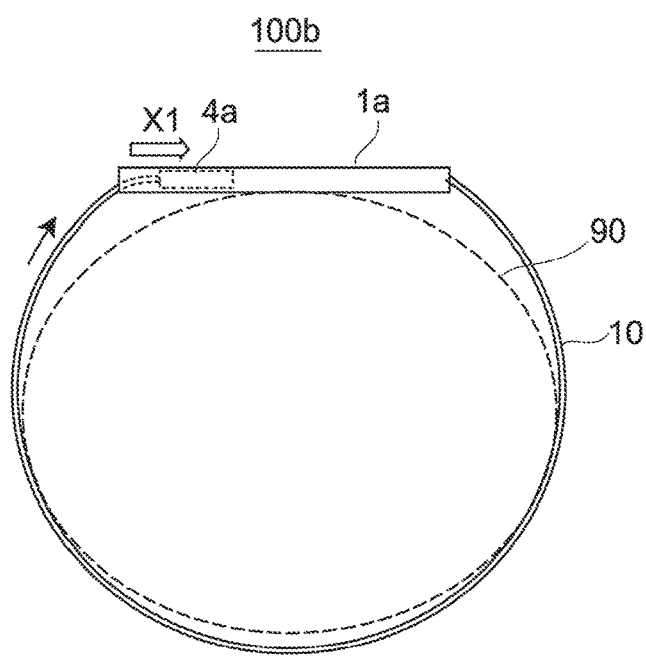

Although the wearable apparatus 100a configured by using the plurality of actuators 1, 1a has been described above, it is possible to configure the wearable apparatus 100a that is capable of giving similar tactile stimulation to a user by using one actuator 1a as shown in FIG. 14, for example. Note that although FIG. 14 shows the case where the actuator 1a that gives tactile stimulation caused by a feeling of tightness is used, it goes without saying that it may be replaced with the actuator 1 that gives tactile stimulation caused by a feeling of pressure.

Figure 15:
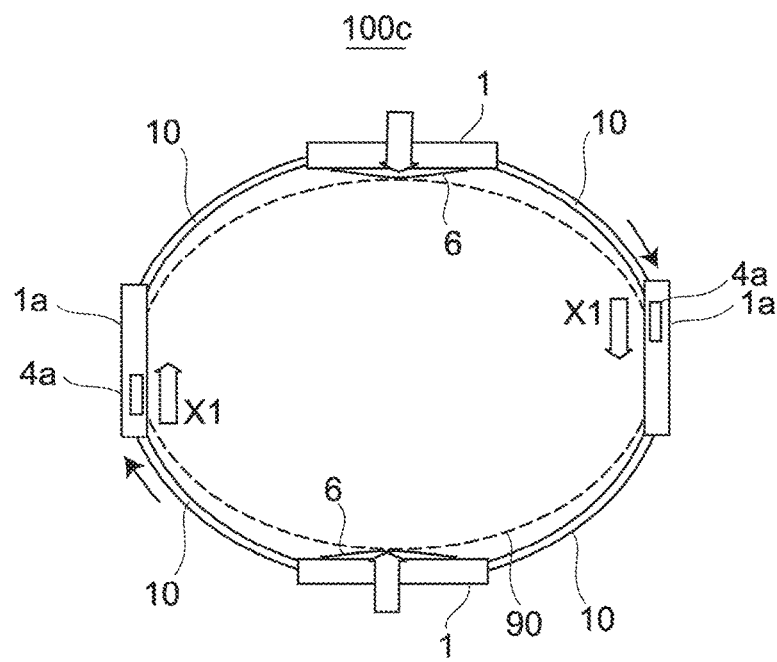
FIG. 15 An overall side view of a wearable apparatus 100c configured by using the actuator 1 that gives tactile stimulation caused by a feeling of pressure and the actuator 1a that gives tactile stimulation caused by a feeling of tightness.

Further, as shown in FIG. 15, a wearable apparatus 100c may be configured by using the actuator 1 that gives tactile stimulation caused by a feeling of pressure and the actuator 1a that gives tactile stimulation caused by a feeling of tightness. In this case, the controller 102 may perform control so that driving current is supplied to the actuator 1 that gives tactile stimulation caused by a feeling of pressure and the actuator 1a that gives tactile stimulation caused by a feeling of tightness at the same time or driving current is supplied at a shifted timing.

Note that the present technology is not limited to the above-mentioned actuators 1, 1a that use the shape-memory alloy. For example, an actuator based on another operating principle such as an electromagnetic linear motor and a piezoelectric linear motor may be used.

[Description of Behavior and Operation]

In the following description, "the wearable apparatus 100 according to this embodiment" represents any one of the above-mentioned wearable apparatuses 100a, 100b, and 100c.

(1. Regarding Variation of Tactile Stimulation)

Because the wearable apparatus 100 according to this embodiment described above employs the actuators 1, 1a that linearly drive the movable portion, it is possible to provide many variations of movement of the movable portion as compared with the case where a rotary driving-based actuator such as an eccentric motor is used.

For example, the following parameters can be selected:
A. Time (Speed) of one stimulation;
B. Strength of one stimulation;
C. Number of times of stimulation;
D. Interval of stimulation;
E. Rhythm of stimulation; and
F. Combination of two or more parameters described above.

Further, in the case where a plurality of actuators are used, information can be assigned also to the following conditions:
G. Which actuator is driven; and
H. In what order actuators are driven.

Further, in the case where a plurality of actuators having different kinds of tactile stimulation are used as shown in FIG. 15, information can be assigned also to the following conditions:
I. Which kind of actuator is driven; and
J. In which kind of order actuators are driven.

Figure 16:
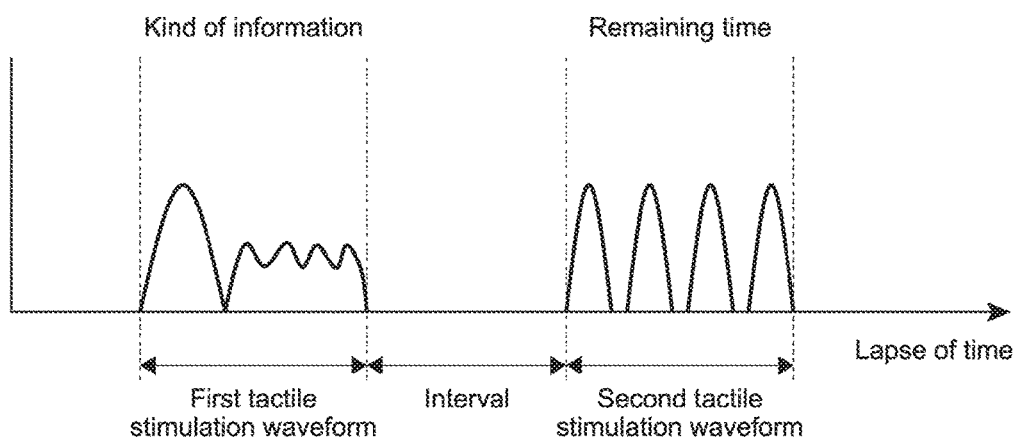
FIG. 16 A diagram expressing the tactile stimulation given to a user by the wearable apparatus 100 with the waveform of driving current supplied to the actuator.

FIG. 16 is a diagram expressing the tactile stimulation given to a user by the wearable apparatus 100 according to the above-mentioned embodiment with the waveform of driving current supplied to the actuator.

This waveform includes a preceding first tactile stimulation waveform and a second tactile stimulation waveform caused at a predetermined interval after the first tactile stimulation waveform. Specifically, in this waveform, the preceding first tactile stimulation and the subsequent second tactile stimulation are transmitted to a user as different tactile stimulation because there is an appropriate interval between them.

The preceding first tactile stimulation waveform includes, for example, a waveform for one pressure feeling stimulation and a waveform for subsequent one tightness stimulation. The second tactile stimulation waveform includes, for example, a waveform for a plurality of times of pressure feeling stimulation. These waveforms are each only a specific example, and what information or meaning is assigned to the parameter of the waveform can be arbitrarily determined. For example, the first tactile stimulation waveform may be a waveform for one pressure feeling stimulation, and the second tactile stimulation waveform may be a waveform for one pressure feeling stimulation similarly.

(2. Application to Alarm Apparatus)

This wearable apparatus 100 can be used as an alarm apparatus for managing the schedule of a user, for example.

For example, a kind of schedule is assigned to the first tactile stimulation waveform. The kind of schedule represents a category for classifying schedule, such as "work," "House," "Play," "Child," and "Parents." This assignment may be performed by a user. The method of assigning the first tactile stimulation waveform to the kind of schedule will be described later.

On the other hand, to the second tactile stimulation waveform, the remaining time before the time and date of an event is assigned, for example. The remaining time before the time and date of an event represents the difference between the time and date at which the event is going to occur and the present time and date. In the second tactile stimulation waveform, parameters such as number of times of stimulation, time, and speed are automatically changed depending on the remaining time before the time and date of an event. For example, as the remaining time before the time and date of an event is reduced, the number of times of stimulation is increased or the time is increased. The user can intuitively recognize that the time and date of an event gradually approaches through the change in stimulation. Note that the example of FIG. 16 shows the case where the remaining time before the time and date of an event is reflected on the number of times of stimulation in the second tactile stimulation waveform.

That is, the user can recognize the occurrence of information and the kind of schedule by receiving the preceding first tactile stimulation, and recognize how much the time and date of an event related to the kind of schedule has approached by receiving the second tactile stimulation caused at a predetermined interval.

Some users divide the importance of related events depending on the kind of schedule. Therefore, when the user recognizes that it is notification of important information by the first tactile stimulation, the user can pay attention to the subsequent second tactile stimulation, for example.

Figure 17:
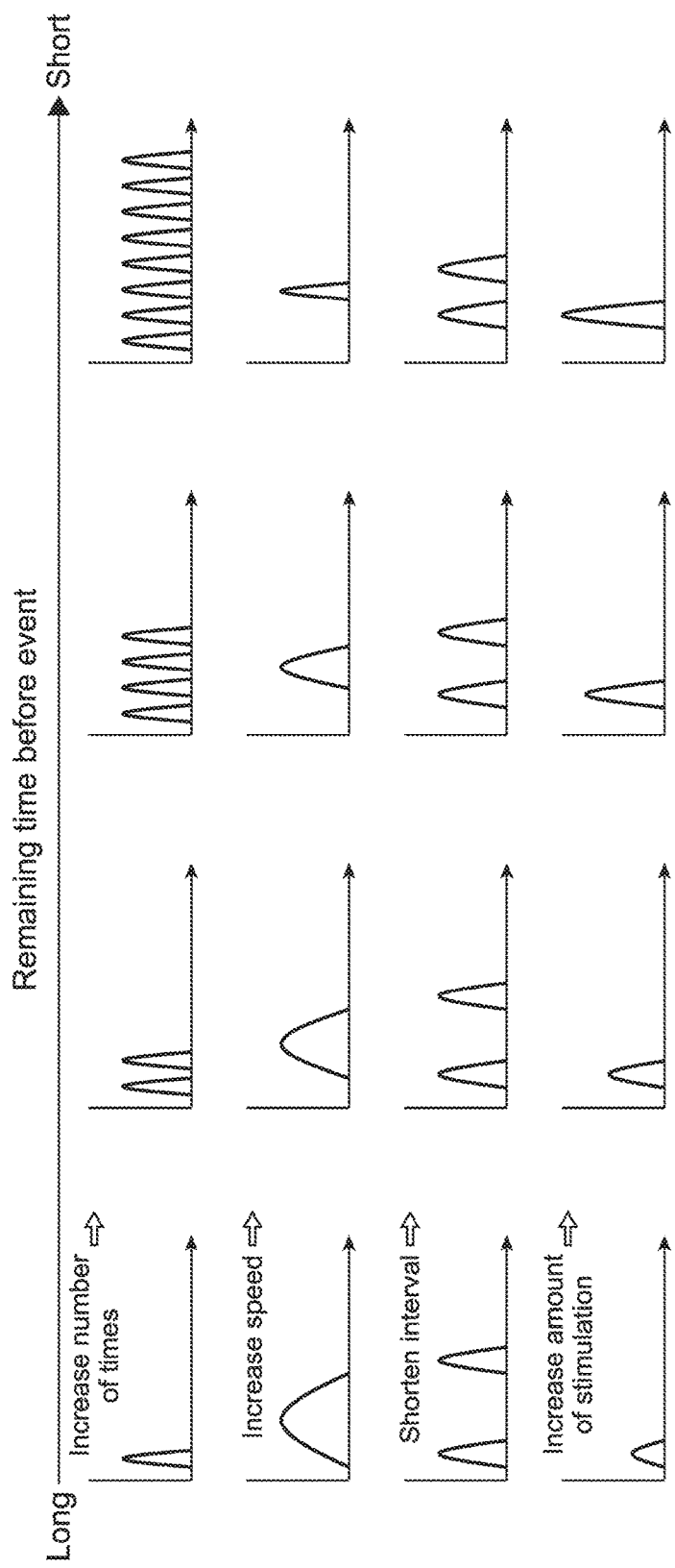
FIG. 17 A diagram showing an example of a change in a second tactile stimulation with a decrease in the remaining time before the time and date of an event.

FIG. 17 is a diagram showing an example of a change in the second tactile stimulation with a decrease in the remaining time before the time and date of an event.

As shown in the figure, examples of the method of changing the second tactile stimulation with a decrease in the remaining time before the time and date of an event include a method of increasing the number of times of stimulation, a method of increasing the acceleration of stimulation, a method of shortening the interval of stimulation, and a method of increasing the strength of stimulation. Which method is employed may be fixed for each kind of schedule, or selected by a user, for example.

(3. Regarding Alarm Setting)

Next, various kinds of setting necessary for the user to receive notification of information by using the above-mentioned first tactile stimulation and second tactile stimulation will be described.

This setting is performed in the information processing terminal of the user, which is capable of communicating with the wearable apparatus 100 according to this embodiment.

The information processing terminal includes a hardware configuration of a computer such as a CPU, a memory, an input device, a display device, a communication unit, and a storage device.

In the memory, an application program for causing the CPU to execute processing necessary for setting the alarm setting information in the wearable apparatus 100 and the like are stored.

The CPU causes the display device to display, for example, setting screen for initial setting information or setting screen for schedule information in accordance with the application program. The CPU generates initial setting information or schedule setting information by processing various kinds of information or commands input from the input device used by a user, and uses the communication unit to transmit it to the wearable apparatus 100 according to this embodiment through wireless or wired communication.

The setting includes initial setting and schedule setting that can be performed at any time.

First, the initial setting will be described.

The initial setting information includes, for example, the following items:
1. First tactile stimulation to the kind of schedule; and
2. Alarm start remaining time and alarm generation time interval.

The method of changing the second tactile stimulation is set as a default.

Figure 18:
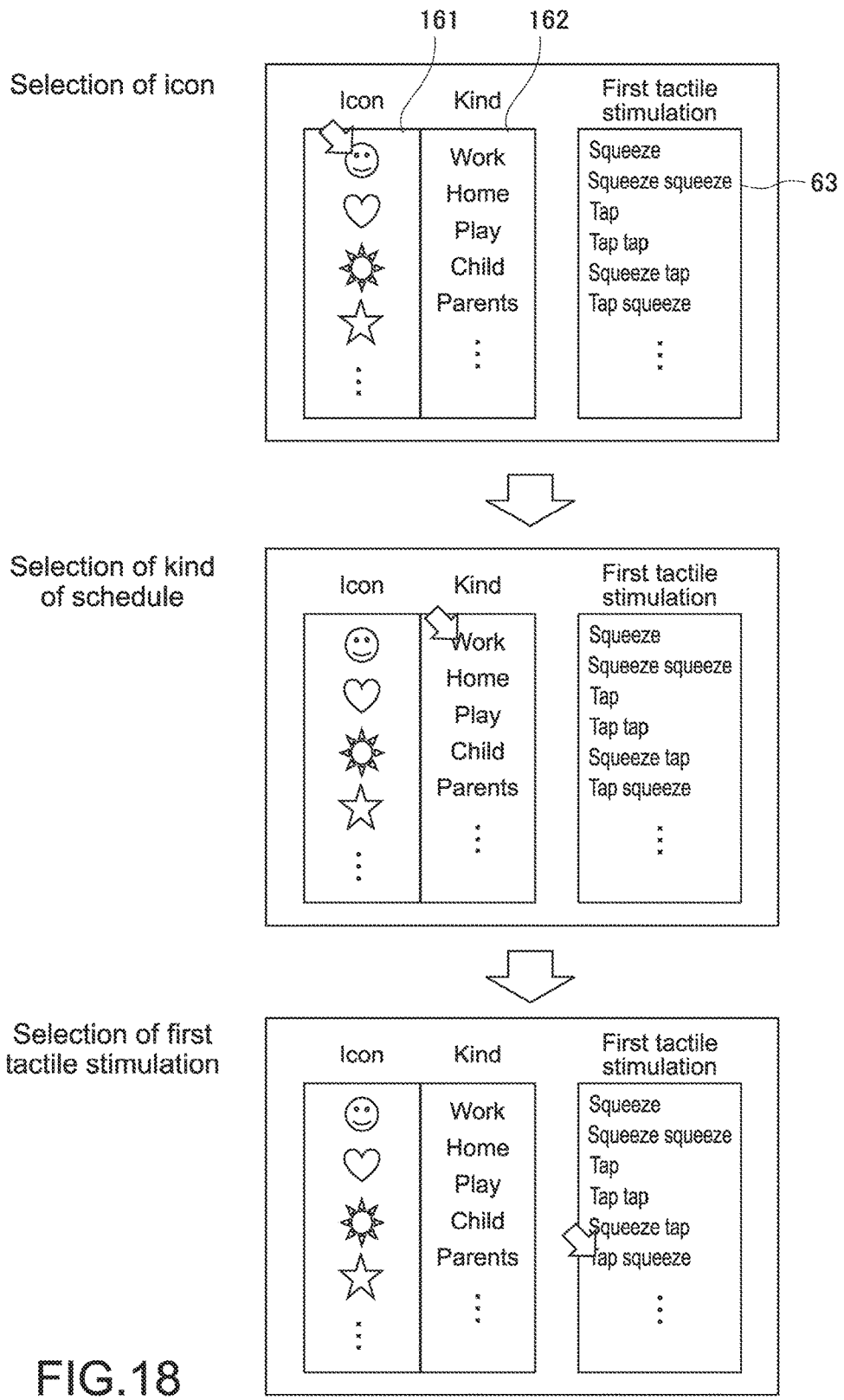
FIG. 18 A diagram showing a setting screen for assigning a first tactile stimulation to the kind of schedule.

FIG. 18 is a diagram showing a setting screen for assigning the first tactile stimulation to the kind of schedule.

To this setting screen, an icon selection area 161, a selection area 162 for the kind of schedule, and a selection area 63 for the first tactile stimulation are provided.

In this setting screen, the user first selects a favorite icon from the icon selection area 161, the kind of arbitrary schedule from the selection area 162 for the kind of schedule, and then favorite first tactile stimulation from the selection area 63 for the first tactile stimulation. The CPU associates pieces of information on the icon, kind of schedule, and first tactile stimulation selected by the user with each other, and stores in the memory as a set of "user setting information related to the first tactile stimulation."

Note that on the selection area 63 for the first tactile stimulation, words for expressing the first tactile stimulation are displayed. Here, "squeeze" represents the feeling of tightness. "Tap" represents the feeling of pressure. Therefore, for example, "Tap squeeze" represents the first tactile stimulation shown in FIG. 16. Instead of such expressions using words, waveforms may be displayed. Further, the wearable apparatus 100 may execute the first tactile stimulation selected by the user from the selection area 63 for the first tactile stimulation so that the user may determine the favorite first tactile stimulation through actual experience of the first tactile stimulation.

Next, the alarm start remaining time and alarm generation time interval, which is another target of the initial setting, will be described.

The user can set information on the remaining time before generation of the first alarm (alarm start remaining time) for the time and date of an event during the initial setting. This alarm start remaining time is, for example, information such as 1 hour ago, 1 day ago, and 1 week ago for the time and date of an event. The user can specify information related to the time interval for repeatedly generating alarm (information on the alarm generation time interval) with the setting of this alarm start remaining time. This information on the alarm generation time interval is, for example, information for specifying the number of temporal division of "1 day," which is the interval of generation of alarm, in the case where the alarm start remaining time is "1 day."

Figure 19:
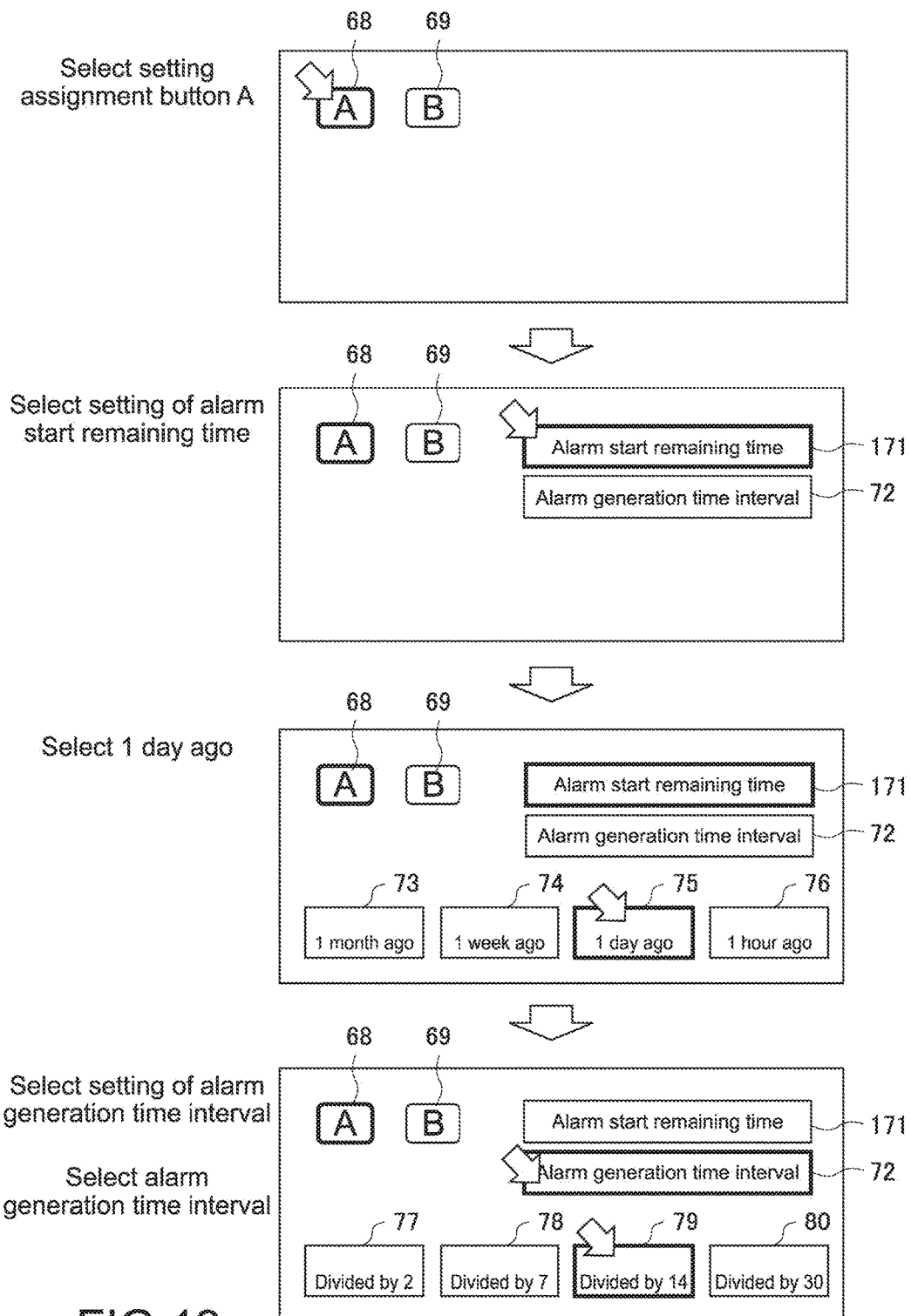
FIG. 19 A diagram showing a setting screen for alarm start remaining time and alarm generation time interval.

FIG. 19 is a diagram showing a setting screen for the alarm start remaining time and the alarm generation time interval.

On the first setting screen, a plurality of alarm assignment buttons 68 and 69 are displayed. In the example of FIG. 19, the alarm assignment button 68 represented by "A" and the alarm assignment button B represented by "B" are displayed. Note that the number of alarm assignment buttons may be three or more.

The user selects any of the alarm assignment buttons (68 or 69) in this setting screen. When the alarm assignment button (68 or 69) is selected, the CPU displays a setting instruction button 171 for the alarm start remaining time and a setting instruction button 72 for the alarm generation time interval. Here, assumption is made that the user selects the setting instruction button 171 for the alarm start remaining time. When receiving this selection, the CPU displays options 73 to 76 for the alarm start remaining time on the setting screen. When the user selects a desired alarm start remaining time, the CPU of the information processing terminal combines the information on the selected alarm start remaining time with information on the selected alarm assignment button, and stores it in the memory or the like.

Next, the user operates the setting instruction button 72 for the alarm generation time interval. When receiving this selection, the CPU displays options 77 to 80 for the alarm generation time interval in the setting screen. When the user selects a desired alarm generation time interval, the CPU of the information processing terminal associates the information on the selected alarm generation time interval with the information on the alarm assignment button and the information on the alarm start remaining time that have already been stored in the memory, and stores it in the memory or the like.

Accordingly, information on the alarm assignment button, information on the alarm start remaining time, and information on the alarm generation time interval are generated as a set of "user setting information related to the second tactile stimulation."

Incidentally, in the setting screen in FIG. 19, the number of division is displayed as a candidate of the alarm generation time interval. Specifically, the time obtained by dividing the alarm start remaining time into N is generated as the alarm generation time interval. However, it is not limited thereto, and the value of the actual time interval may be displayed.

(4. Schedule Setting)

Next, the method of setting the schedule information will be described.

Figure 20:
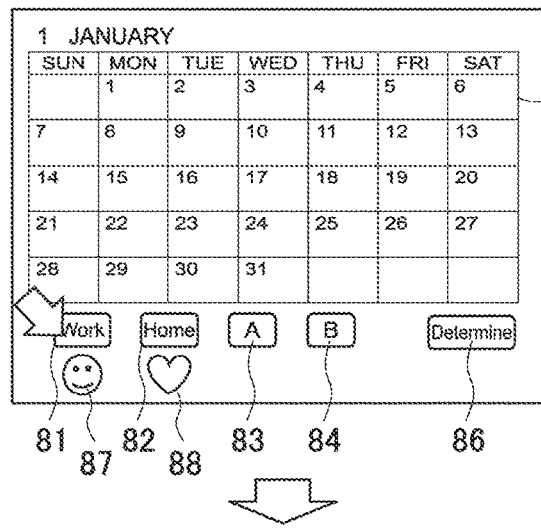
FIG. 20 A diagram showing a schedule setting screen.
Figure 20:
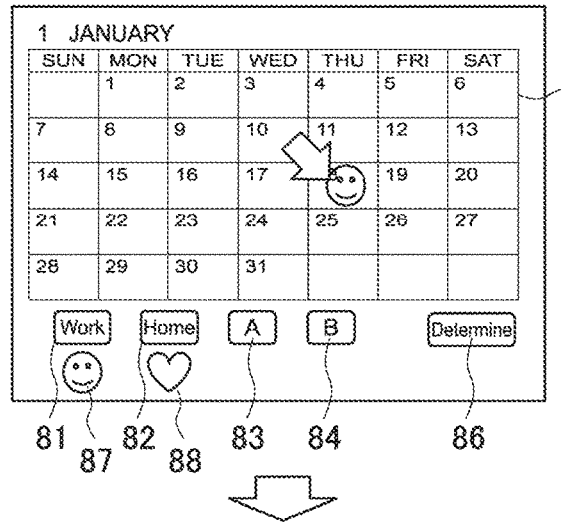
Figure 20:
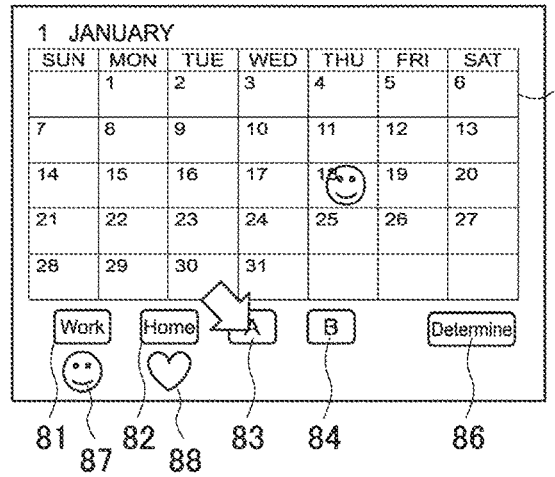

FIG. 20 is a diagram showing the schedule setting screen.

On the schedule setting screen, schedule-kind selection button 81 and 82, alarm assignment buttons 83 and 84, a calendar 85, and a determination button 86 are provided.

The schedule-kind selection buttons 81 and 82 are associated with the user setting information related to the first tactile stimulation. On the schedule-kind selection buttons 81 and 82, the kind of corresponding schedule is written. Further, the schedule-kind selection buttons 81 and 82 are displayed in association with icons 87 and 88 assigned to the kind of the schedule.

First, the user uses the input apparatus to operate the schedule-kind selection button (81 or 82) corresponding to the kind of schedule that is desired to be set in the schedule setting screen. Next, the user selects the date in the calendar 85 corresponding to the time and date of an event of the schedule that is desired to be set. This selection of the date in the calendar 85 is performed by, for example, using the input apparatus to perform drag and drop operation on the icon 87.

Next, the user inputs a detailed time and date of an event in an event-time-and-date detail setting screen (not shown) for the selected date. Then, the user selects the alarm assignment button (83 or 84) to which the desired user setting information related to the second tactile stimulation is assigned. Then, the user operates the determination button 86 lastly, and thus, the user's input operation for setting the schedule information is finished.

The CPU of the information processing terminal temporarily stores the user setting information related to the first tactile stimulation associated with the schedule-kind selection button (81 or 82) operated by the user in the schedule setting screen, the input time and date of an event, and the user setting information related to the second tactile stimulation assigned to the operated alarm assignment button (83 or 84) as a whole entity of the alarm setting information in a memory or the like.

After that, the CPU of the information processing terminal transmits the alarm setting information stored in the memory or the like to the wearable apparatus 100 by using the communication unit, and stores it in the memory 112 of the controller 102 of the wearable apparatus 100.

(5. Regarding Alarm Emission Processing in Actuator 1 Unit)

Next, alarm emission processing performed by the controller 102 of the wearable apparatus 100 according to this embodiment will be described.

In the controller 102 of the wearable apparatus 100, the CPU 111 generates a timing of emitting alarm on the basis of the current time and date of the timer 113 and the alarm setting information. Specifically, the CPU 111 calculates a recent time and date of emitting alarm on the basis of the time and date of an event included in the alarm setting information and the user setting information related to the second tactile stimulation. Then, the CPU 111 determines that it is a timing of emitting alarm when the current time and date of the timer 113 matches with the recent time and date.

Note that the recent time and date that is the first evaluation target is a time and date obtained by subtracting the alarm start remaining time included in the user setting information related to the second tactile stimulation from the time and date of an event. The recent time and date that is the next evaluation target is obtained by adding the alarm generation time interval included in the user setting information related to the second tactile stimulation to the recent time and date that is the first evaluation target.

When determining the timing of emitting alarm, the CPU 111 generates waveform information of the first tactile stimulation on the basis of information on the first tactile stimulation included in the alarm setting information. Next, the CPU 111 calculates the remaining time before the time and date of an event on the basis of the user setting information related to the second tactile stimulation included in the alarm setting information, and generates waveform information of the second tactile stimulation on the basis of the remaining time. The CPU 111 temporarily couples the waveform information of the first tactile stimulation and the waveform information of the second tactile stimulation to each other to generate one piece of waveform information.

Then, the CPU 111 outputs a control signal to the driving circuit 103 so that driving current corresponding to the waveform information is supplied to the actuator 1 (1a). Accordingly, the actuator 1 (1a) is driven, and alarm caused by tactile stimulation is provided to the user.

<First Modified Example>

Next, a modified example of the embodiment will be described.

Figure 21:
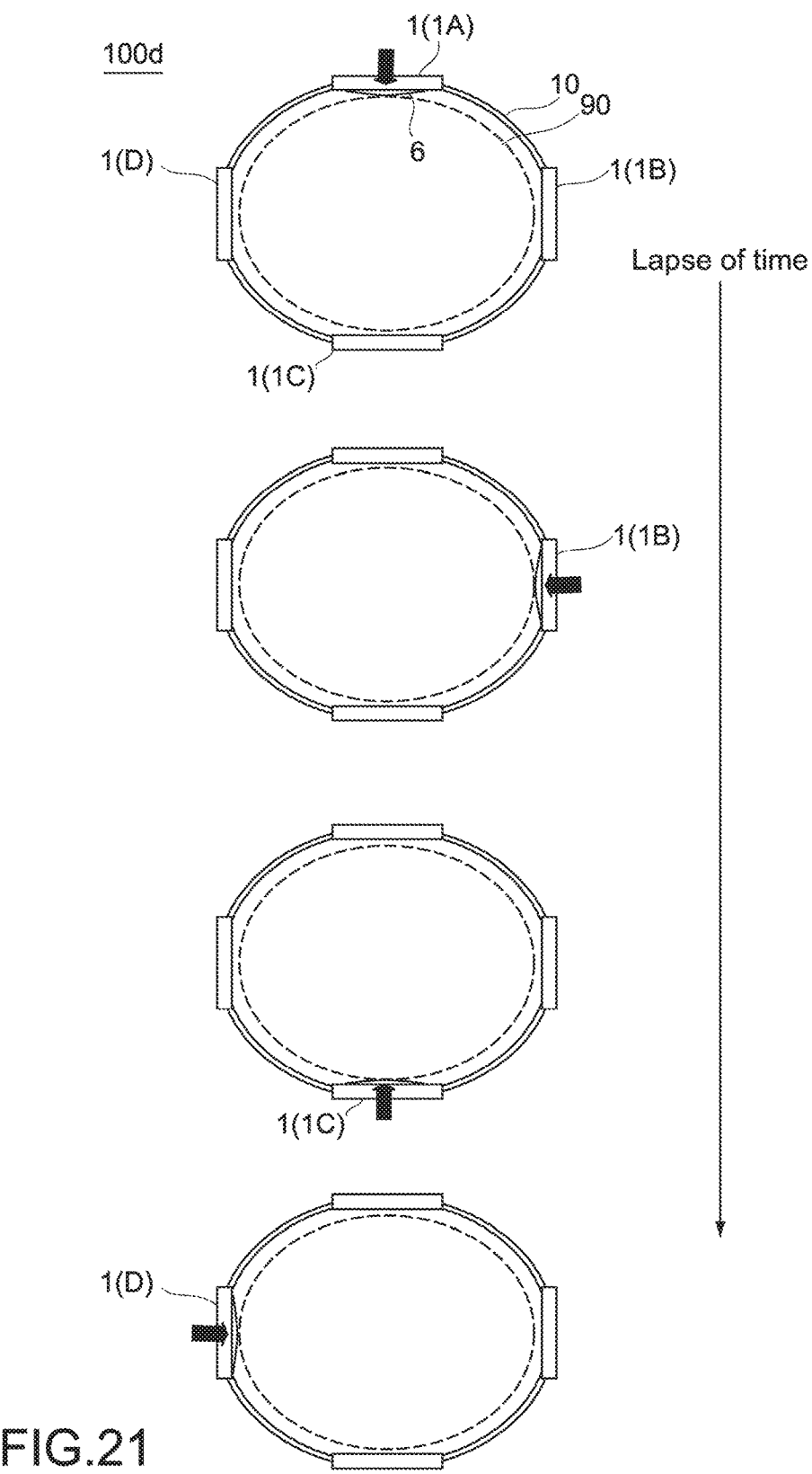
FIG. 21 A diagram for describing a wearable apparatus 100d according to a first modified example.

FIG. 21 is a diagram for describing a wearable apparatus 100d according to a first modified example.

In this wearable apparatus 100d, driving timing of a plurality of actuators 1 (actuator 1A, actuator 1B, actuator 1C and actuator 1D) is shifted.

The plurality of actuators 1 (actuator 1A, actuator 1B, actuator 1C and actuator 1D) are driven in the order of being coupled via the belt 10 in series, e.g., in the clockwise direction in the figure. Alternatively, they may be sequentially driven in the counterclockwise direction in the figure.

The periods in which two adjacent actuators are driven may partially overlap with each other, or do not need to overlap. Alternatively, they may be driven across an interval.

Further, they may be driven with driving current corresponding to the waveform information different for each actuator 1.

The number, time, strength, and speed of waveforms of driving current supplied to the actuators 1, and the interval of current supply to the actuators may be optimized so that the speed of movement of the position at which tactile stimulation is given is gradually increased or decreased in the order of the actuator 1A, the actuator 1B, the actuator 1C, and the actuator 1D, or in the opposite order.

By the wearable apparatus 100d according to the modified example, it is possible to provide various pieces of information to the user through the movement of a position of tactile stimulation.

Note that as an actuator, not only an actuator that gives tactile stimulation caused by a feeling of pressure but also an actuator that gives tactile stimulation caused by a feeling of tightness can be used.

It should be noted that the present technology may take the following configurations.

(1) An information presentation apparatus, including:

an actuator that includes a movable portion and is capable of linearly driving the movable portion;

a control unit that controls the actuator so that the movable portion is driven corresponding to waveform information; and a belt for attaching the actuator to a user.

(2) The information presentation apparatus according to (1) above, in which an end portion of the belt is fixed to the movable portion, and a length of a portion of the belt is changed by driving of the movable portion in a forward or backward direction, the portion being wrapped around the user, (3) The information presentation apparatus according to (1) or (2) above, further including a communication unit that acquires setting information through communication, the setting information including at least stimulation-type information for identifying a kind of the tactile stimulation, in which the control unit is configured to generate the waveform information on the basis of the stimulation-type information included in the acquired setting information.

(4) The information presentation apparatus according to (3) above, in which the setting information further includes temporal setting information, and the control unit is configured to generate a timing of driving the movable portion on the basis of the temporal setting information included in the acquired setting information.

(5) The information presentation apparatus according to (1) above, further including a pressing portion that is freely movable forward and backward in approaching and separating directions with respect to an attached portion of the user in synchronization with the movable portion.

(6) The information presentation apparatus according to (5) above, further including a communication unit that acquires setting information through communication, the setting information including at least stimulation-type information for identifying a kind of the tactile stimulation, in which the control unit is configured to generate the waveform information on the basis of the stimulation-type information included in the acquired setting information.

(7) The information presentation apparatus according to (5) or (6) above, in which the setting information further includes temporal setting information, and the control unit is configured to generate a timing of driving the movable portion on the basis of the temporal setting information included in the acquired setting information.

REFERENCE SIGNS LIST 1 actuator
1a actuator
4 slider
4a slider
5 shape-memory alloy wire
6 elastic plate
10 belt
100 wearable apparatus
100a wearable apparatus
101 communication unit
102 controller
103 driving circuit
111 CPU
112 memory
113 timer

The invention claimed is:

1. An information presentation apparatus, comprising:
an actuator that includes a movable portion, wherein the actuator is configured to linearly drive the movable portion in a forward and backward direction;
a control unit configured to control the actuator based on waveform information, wherein the movable portion is linearly driven corresponding to the waveform information; and
a belt to attach the actuator to a user, wherein an end portion of the belt is fixed to the movable portion,
wherein the actuator is further configured to linearly drive the movable portion to change a length of a portion of the belt, and
wherein the portion of the belt is wrapped around the user.

2. The information presentation apparatus according to claim 1, further comprising:
a communication unit configured to acquire setting information from an information processing terminal via communication, wherein the setting information includes stimulation-type information to identify a type of a tactile stimulation,
wherein the control unit is further configured to generate the waveform information based on the stimulation-type information included in the acquired setting information.

3. The information presentation apparatus according to claim 2, wherein
the setting information further includes temporal setting information, and
the control unit is further configured to generate timing information to linearly drive the movable portion based on the temporal setting information.

4. The information presentation apparatus according to claim 2, wherein the type of the tactile stimulation includes at least one of a pressed tactile sense, rubbed tactile sense, hit tactile sense, or tightened tactile sense.

5. The information presentation apparatus according to claim 1,
wherein the actuator further comprises a pressing portion, wherein the pressing portion moves in the forward and backward direction to approach and separate with respect to an attached surface of a body of the user, and
wherein the pressing portion moves in synchronization with the movable portion.

6. An information presentation apparatus, comprising:
a plurality of actuators, wherein each of the plurality of actuators includes a movable portion, and wherein each of the plurality of actuators is configured to linearly drive the respective movable portion in a forward and backward direction;
a control unit configured to control the plurality of actuators based on waveform information, wherein the respective movable portion of each of the plurality of actuators is driven corresponding to the waveform information; and
a belt to attach the plurality of actuators to a user,
wherein each of the plurality of actuators is further configured to linearly drive the respective movable portion to change a length of a portion of the belt, and
wherein the portion of the belt is wrapped around the user.

7. The information presentation apparatus according to claim 6, wherein
the belt comprises a plurality of coupling belts to couple the plurality of actuators in series, and
wherein an end portion of each of the plurality of coupling belts is fixed to the respective movable portion of each of the plurality of actuators.

8. The information presentation apparatus according to claim 7, wherein the control unit is further configured to linearly drive the plurality of actuators in an order of the plurality of actuators coupled in series by the plurality of coupling belts.

9. The information presentation apparatus according to claim 6, wherein each of the plurality of actuators further includes a pressing portion, wherein the pressing portion moves in the forward and backward direction to approach and separate with respect to an attached surface of a body of the user, and wherein the pressing portion moves in synchronization with the movable portion.

10. The information presentation apparatus according to claim 9, wherein the control unit is further configured to drive the plurality of actuators in an order in which the plurality of actuators are coupled in series by the belt.

* * * * *